United States Patent
Los

(10) Patent No.: US 9,918,941 B2
(45) Date of Patent: Mar. 20, 2018

(54) METHOD FOR PRODUCING ENTERIC ALGINATE MICROCAPSULES VIA IONIC GELATION CONTAINING DICLOFENAC OR ONE OF THE SALTS THEREOF AND MULTIPARTICLED PHARMACEUTICAL COMPOSITION CONTAINING THEM

(71) Applicants: Eastbrand Holding GMBH, Vienna (AT); Laboratories Bagó S.A., Buenos Aires (AR)

(72) Inventor: Mario Atilio Los, Buenos Aires (AR)

(73) Assignees: Laboratorios Bago S.A., Buenos Aires (AR); Eastbrand Holding GMBH, Vienna (AT)

( * ) Notice: Subject to any disclaimer, the term of this patent is extended or adjusted under 35 U.S.C. 154(b) by 0 days.

(21) Appl. No.: 15/454,127

(22) Filed: Mar. 9, 2017

(65) Prior Publication Data
US 2017/0172934 A1 Jun. 22, 2017

Related U.S. Application Data

(62) Division of application No. 14/386,377, filed as application No. PCT/EP2012/054904 on Mar. 20, 2012, now Pat. No. 9,668,978.

(51) Int. Cl.
| | |
|---|---|
| *A61K 9/50* | (2006.01) |
| *A61K 9/20* | (2006.01) |
| *A61K 9/14* | (2006.01) |
| *A61K 31/4439* | (2006.01) |
| *A61K 31/196* | (2006.01) |
| *A61K 47/36* | (2006.01) |

(52) U.S. Cl.
CPC ............. *A61K 9/5036* (2013.01); *A61K 9/14* (2013.01); *A61K 9/20* (2013.01); *A61K 31/196* (2013.01); *A61K 31/4439* (2013.01); *A61K 47/36* (2013.01)

(58) Field of Classification Search
None
See application file for complete search history.

(56) References Cited

U.S. PATENT DOCUMENTS

| | | | | |
|---|---|---|---|---|
| 5,711,967 A | * | 1/1998 | Juch | A61K 9/5078 424/461 |
| 6,096,344 A | * | 8/2000 | Liu | A61K 9/1652 264/4.33 |
| 6,544,556 B1 | * | 4/2003 | Chen | A61K 9/209 424/451 |
| 2006/0188565 A1 | * | 8/2006 | Reiner | A61K 9/2009 424/451 |

FOREIGN PATENT DOCUMENTS

| | | |
|---|---|---|
| EP | 0635261 A1 | 1/1995 |
| WO | WO-9725064 A1 | 7/1997 |

OTHER PUBLICATIONS

Gonzalez-Rodriguez et al., "Alginate/chitosan particulate systems for sodium diclofenac release", International Journal of Pharmaceutics, 232 (2002), pp. 225-234.*
Gonzalez-Rodriguez et al., Alginate/Chitosan Particulate Systems for Sodium Diclofenac Release, International Journal of Pharmaceutics 232, 2002), pp. 225-234.
International Search Report & Written Opinion for PCT/EP2012/054904, dated Nov. 26, 2012.

* cited by examiner

*Primary Examiner* — Carlos A Azpuru
*Assistant Examiner* — Casey S Hagopian
(74) *Attorney, Agent, or Firm* — Dinsmore & Shohl LLP

(57) ABSTRACT

Method for producing enteric microcapsules without coating, containing diclofenac or one of the salts thereof with satisfactory anti-inflammatory activity and low gastric aggressiveness; and a pharmaceutical composition containing them. The method comprises a) preparing a mixture in water-ethanol with an alginate salt, adding diclofenac or one of the salts thereof previously diluted with a surfactant and sodium bicarbonate; b) adding the previous solution to a solution with a calcium salt; c) resuspending the microcapsules obtained and isolated in an aqueous solution of the alginate salt; and d) isolating, drying and sieving through 1000 and 250 micron meshes the microcapsules obtained; and selecting the fraction comprised between both meshes. The pharmaceutical composition can be an oral composition, tablets, chewable tablets, or a powder for suspension in water.

13 Claims, No Drawings

METHOD FOR PRODUCING ENTERIC ALGINATE MICROCAPSULES VIA IONIC GELATION CONTAINING DICLOFENAC OR ONE OF THE SALTS THEREOF AND MULTIPARTICLED PHARMACEUTICAL COMPOSITION CONTAINING THEM

REFERENCE TO RELATED APPLICATIONS

This application is a divisional of U.S. patent application Ser. No. 14/386,377, filed Nov. 25, 2014, which is a U.S. national stage of PCT/EP2012/054904, filed Mar. 20, 2012, the entire content of both of which is incorporated herein by reference.

FIELD OF THE INVENTION

The aim of this invention is a novel method, applicable to industry for producing enteric microcapsules without a coating, containing diclofenac or one of the salts thereof of oral use (sodium, potassium, epolamine) with satisfactory anti-inflammatory behaviour and low gastric aggressiveness; and a pharmaceutical composition containing them.

The pharmaceutical composition containing the said enteric microcapsules (which determine local mucus protection) exists in the form of oral capsules, tablets, chewable tablets, or powder for suspension in water prior to being administered to a patient.

The invention also relates to pharmaceutical compositions containing enteric microcapsules without coating aggregates, diclofenac aggregates associated with proton pump inhibitors (for example, omeprazole) that are known industrially and are available in the form of enteric pellets in a novel, oral pharmaceutical composition that contains both active ingredients in the same composition.

BACKGROUND OF THE INVENTION

The 2-((2,6 dichlorophenyl)amino)phenyl acetic (diclofenac) acid (CAS No 15307-86-5) is a nonsteroidal anti-inflammatory drug (NSAID) with analgesic, anti-inflammatory and antipyretic activity.

Diclofenac and the salts thereof are frequently used in human medicine in the form of coated tablets or oral capsules.

The salts are characterized by their bitter, unpleasant taste and strong astringency.

Also, they generally have significant side effects such as nausea, epigastric pains, vomiting, diarrhoea and gastric irritation, with medical surveillance being particularly advisable for patients with a history of peptic ulcers and gastrointestinal bleeding.

Preventing the above-mentioned adverse and frequent gastrointestinal side effects of nonsteroidal anti-inflammatory drugs is particularly important. In that it is independent of the treatment time and more important in risk groups such as Patients over 60 years old
Patients with a history of peptic ulcers
Patients treated with corticosteroids or anticoagulants
Patients with a history of alcoholism and/or smoking
  (Arya N., Rossos P. G., Geriatrics & Agentes 2002; 5 (10); 28-31).

Consequently, it is necessary to have an orally administered composition that includes diclofenac or one of the salts thereof, but with the particular characteristic of providing local mucus protection in the stomach, as well as levels of diclofenac or convenient anti-inflammatory and analgesic activity.

Historically, literature has highlighted the aggressiveness of nonsteroidal anti-inflammatory drugs. It has even shown that the simultaneous use of two pharmaceutical compositions, each containing a proton pump inhibitor (omeprazole) and a nonsteroidal anti-inflammatory drug, reduces the occurrence of ulcers in patients (Hawkey C. J. et al; N. Engl., J. Med. 1998; 338; 727-34: Yeomans N. D. et al, N. Engl., J. Med 1998; 338, 719-26). Ratifying the need to protect the gastric mucus from the considerable aggressiveness caused by nonsteroidal anti-inflammatory drugs.

Pharmaceutical technology has resolved numerous problems associated with producing oral pharmaceutical compositions using techniques applied previously to the pure active ingredients containing them.

The methods used with the pure active ingredients enable: protecting substances against humidity, preventing oxidation, masking the taste and smell of substances which, in organoleptic terms, are unpleasant, improving the stability of pharmaceutical compositions, modifying the release speed of active ingredients and others.

The methods used have been numerous, heterogeneous and dependent on the physical-chemical properties of the active ingredient in question.

In a non-limiting manner, they can be classified as a) Physical-chemical methods, such as for example, microencapsulation through solvent evaporation; b) Chemical, via gelation of the support material, and others; c) Mechanical, with fluid bed coating, and others.

The number of explored alternatives has been very high. So, for example:

I) One of the alternatives described relates to microencapsulation. The microcapsules are solid products made up of spherical, quasi spherical or irregular shaped polymers, sized between 100 and approximately 1000 micron and containing ingredients that are pharmacologically active.

Generally, a microencapsulation method with optimum characteristics requires the strict control of a large number of parameters.

J. B. Deasy (J. Microencapsulation, 1994, Vol. II, No 5, 487-505) and A. K. Dash (J. Microencapsulation, 1997, Vol. 14, No 1, 101-112) have described some factors that condition the characteristics or properties of the products obtained by microencapsulation such as: size, content and release speed of the substances with pharmacological activity that they contain. The microcapsule characteristics or properties are associated with several factors. For example:
  a) The production method,
  b) Composition,
  c) The solubility of the active ingredient,
  d) The formation time.

For pharmaceutical use, the formation of the microcapsules obtained from alginic acid, is interesting because of the non toxic nature of the alginic acid, which is non-mutagenic, or immunogenic, and also because of its particular ability to not react with the pharmacologically active ingredients.

By incorporating an aqueous solution of sodium alginate in another solution, also aqueous, of calcium chloride, it is possible to obtain microcapsules via gelation. But the microcapsules that are obtained using this process, usually tend to join together and their size is frequently larger than 1 mm.

II) Another different alternative was the obtention of microparticles described by M. F. Al-Omran et al (J. Microencapsulation 2002, Vol. 19, No. 1, 45-52). It is a method intended to mask the unpleasant taste of diclofenac sodium via evaporation of the solvent contained in the active ingredient and other components. The method is complex and involves two general steps:

A) In the first step, diclofenac sodium cores are prepared via the suspension of diclofenac sodium in acetone-b-hexane, lactose and avicel and the gradual addition of water up to agglomeration.

B) In the second step the microcapsules are prepared by adding the diclofenac sodium cores to a solution of ethyl cellulose in toluene, under stirring (1000 r.p.m.). Beforehand, diethylphlalate or polyethylene glycol 600 are added as plastifying agents (20 to 40% w/w vis-à-vis the weight of ethyl cellulose and petrol ether) gradually until the solution starts to turn cloudy. Also 2% magnesium stearate is added. The microcapsules that are formed are filtered and dried over 24 hours.

The method suffers from various practical drawbacks:

a) It requires two general steps and each one conditions the final characteristics of the microcapsules.

b) It uses organic solvents, which must be completely removed before preparing pharmaceutical formats for human use.

c) The diclofenac content of the microcapsules obtained is very irregular and can vary between 23.1 and 60.1% according to the nature of the cores that are used (diclofenac powder or spherical cores containing diclofenac).

To summarise, it is not a very practical method.

III) In 1998 M. J. Fernandez et al. (International Journal of Pharmaceutical 163 (1998); 23-24) described the production of enteric microcapsules with a heterogeneous composition containing diclofenac, hydroxy ethyl pyrrolidine, calcium alginate and Eudragit L30D and others which, apart from the diclofenac salt, contain alginate and chitosan.

The method described is not very practical in that for both cases it requires incubating at ambient temperature (22° C.) for 24 hours and drying at ambient temperature another 24 hours. The authors highlight that it is necessary to study the influence of various factors (molecular weight of chitosan, chitosan/alginate ratio and interaction of diclofenac salt-chitosan); consequently, it is not a defined method, likely to be applicable to industry. Neither do they describe the production of pharmaceutical compositions.

IV) In 2009 V. N. Deshmukh et al (Researh J. Pham and Tech 2 (2) April-June 2009-p. 324-327) described the production and control of heterogeneous microcapsules comprising calcium alginate and a hydrophilic polymer of the Locus bean type and Xanthan gum with extended release—they do not produce pharmaceutical compositions and the microcapsules obtained suffer from the drawback that the total release of the content requires virtually 12 hours.

V) The literature also describes other different methods for forming microparticles containing diclofenac or the salts thereof. For example, via pelletizing. The pellets obtained are used in the production of pharmaceutical compositions. For example, U.S. Pat. No. 5,800,836 reveals a pharmaceutical formula in the form of delayed action pellets or U.S. Pat. No. 5,711,967 also mentions a pharmaceutical formula in the form of delayed action pellets comprising diclofenac sodium and others.

In all the cases mentioned in the literature for the production of pellets or microgranules via extrusion and spheronization, complex, industrial equipment is used. For example, Marumerizer (Luwa) or CF-Granulator (Vector).

VI) Another different technological alternative for manufacturing useful particles for producing pharmaceutical compositions mentioned in the technical literature includes using neutral starch cores, sugar, microcrystalline cellulose or other substances that are small in size and are covered by atomization with a solution or suspension containing the active ingredient (diclofenac or the salts thereof) together with other components like polymers, fixing agents, plastifying agents, colouring agents and known additives for pharmaceutical use.

This methodology, although interesting, suffers from the drawback of requiring the use of high technology equipment like a fluid bed dryer for atomisation which, generally includes a Wurster system that obliges the movement of the particles and enables them to be coated uniformly with spray. Expensive industrial system that is neither easily nor quickly implemented in industry due to the high number of variables involved, including, the number of components in the coating solution or suspension, flow speed, air pressure, operating temperature, etc. Producing the coated microgranules using this methodology is very complex because of the significant number of variables to be considered in each case and also its industrial implementation is very complex in the scale increase from small scale laboratory to normal production scale. An operation that can determine the success or failure of the implementation.

VII) Patent Application AR No P040100731 (19 May 2004) published on 14 Sep. 2005 under number AR 44.398 Al claims a method of producing heterogeneous microcapsules whose active ingredient is optionally sodium diclofenac, ibuprofen, famotidine or acetylsalicylic acid characterized in that the active ingredient is added dissolved or in suspension (with a particle size between 20 and 120 micron) to a solution containing sodium bicarbonate, sodium alginate and an appropriate surfactant, and the suspension that is formed is dispersed under stirring in an aqueous solution of calcium chloride, producing the formation of microcapsules that separate from each other or are filtered, without previous drying, and are added to an aqueous solution made up of coating agents including sucralose, colouring agent, lactose, hydroxypropyl methylcellulose, triacetin and titanium oxide (see page 5, line to page 6, line 6, claim 9) which confer enteric behaviour and the ability to correct the taste of the microcapsules formed.

The microcapsules obtained have a heterogeneous composition due to the coating applied to them. Their active ingredient content is between 30 and 55% according to the nature of the active ingredient and the enteric coating used in the method.

However this process requires that the shape of the microcapsules obtained be almost perfect spheres with an even particle size so as to obtain a uniform coating.

Consequently, there is a technical void which makes it necessary to provide a practical method for producing microcapsules of diclofenac or one of the salts thereof preferably with a homogeneous composition, that is, which only include in their composition calcium alginate without the need of the enteric coatings aggregate, and which ensures that the microcapsules obtained have, among others, the following characteristics: a) high active ingredient content; b) which do not release the active ingredient at the average stomach acid pH; c) which immediately release the active ingredient they contain at the average intestine pH; d) and physical strength and sufficient stability to enable the production of the chosen pharmaceutical composition; e)

with sufficient plasticity to produce tablets and chewable tablets, which thanks to said plasticity prevent the microcapsules being broken by the pressure applied during the production of these compositions; f) that the microcapsules obtained mask partially or wholly the unpleasant taste of diclofenac or the salts thereof to contribute to the patient's acceptability of the pharmaceutical composition containing them, the indicated dosage and consequently the fulfilment of the treatment; g) that due to their stability they also enable the association with other active ingredients and, in particular, with proton pump inhibitors in the form of pellets, with omeprazole pellets, esomeprazole pellets and lanzoprazole pellets being chosen; h) that their composition only includes sodium alginate obtained via gelation with a soluble calcium salt, and no other additional components.

And above all, that they have the particular characteristic of providing local mucus protection to the stomach and also anti-inflammatory, analgesic activity and appropriate levels of diclofenac.

SUMMARY OF THE INVENTION

A first aim of the invention is to provide a simple method that enables obtaining microcapsules that are resistant to the stomach acid pH in order to avoid the direct aggression of diclofenac or the salts thereof on the stomach mucus. In other words, enteric microcapsules without enteric coating agents aggregate, but with the capacity to release the active ingredient they contain at the intestinal pH.

So, for example, the microcapsules obtained have an homogeneous composition in the sense that their composition only includes sodium alginate. Once obtained, they do not need coating with other components which would give them the characteristic of heterogeneous microcapsules by being enteric and tasteless. In the case of microcapsules with a heterogeneous composition it is necessary to consider the characteristics of the components in the suspension with which the coating is made. It is not enough that the coating gives them the lack of taste and enteric nature. It is necessary that the components of the coating suspension do not affect the stability of the microcapsules.

The possibility of producing microcapsules with enteric character and virtually tasteless with one single component (sodium alginate) is novel, useful and economical.

The non-coated microcapsules obtained according to the process of this invention have shown in vitro and at simulated stomach pH (HCL 0.1 N) during 2 hours and under stirring (50 rpm or 75 rpm) that they do not release a significant amount of the active ingredient they contain. However at the simulated intestinal pH (phosphate buffer pH 6.8) they release a high percentage of their content in 45 minutes. The diclofenac potassium microcapsules obtained revealed a greater release at 75% in 45 minutes at only 50 r.p.m. According to the conditions of Section 2 USP for pharmaceutical formats; while in the microcapsules with enteric coating an active ingredient release rate of between 90% and 100% was achieved, but at a stirring speed of 100 r.p.m.

Such behaviour is particularly useful in that the technical literature highlights that diclofenac and the salts thereof express their aggressiveness on gastric mucus in the stomach at a pH below 4.0 and near 1.0 and are absorbed in the intestine at an approximate pH of 6.8.

The high release percentage at 45 minutes is practically useful for the production of the chosen pharmaceutical composition.

Another objective of this invention relates to the active ingredient content in the microcapsules without coating. It has been revealed that the active ingredient content in the microcapsules produced according to this invention is greater than 50% of the dry weight of said microcapsules, approximately between 55% and 65% on a dry weight basis.

Another objective of this invention is to obtain enteric microcapsules without the need of the enteric coating agent aggregate, with sufficient physical strength to withstand the pressure that is usually applied during the production of the pharmaceutical compositions in the form of capsules, powder for suspension, tablets and even associations with other active ingredients. Production that requires prolonged mixing operations to try and obtain a uniform distribution of the respective components.

Another objective of this invention is that the enteric microcapsules obtained have virtually no bitter, unpleasant taste or strong astringency typical of diclofenac and the salts thereof without the need of coating, once formed. Consequently they are particularly applicable for the production of pharmaceutical compositions which, owing to their nature, require a greater presence in the buccal cavity, such as for example chewable tablets or powder for suspension. The characteristic of significantly masking the taste specifically contributes an additional practical advantage to the enteric behaviour, in that it simplifies the production of pleasant tasting oral pharmaceutical compositions.

Another objective of this invention is to obtain microcapsules of diclofenac or the salts thereof with sufficient physical and chemical stability to be associated subsequently with other active ingredients.

Another objective of this invention that is of practical importance and novel relates to the plasticity that the microcapsules possess. Said plasticity enables the microcapsules to withstand the mechanical pressure that has to be applied to produce tablets and chewable tablets, without causing them to be broken due to the pressure applied. This characteristic is generally absent in the pellets.

Another objective of this invention is to select enteric microcapsules during the production with a particle size scope that minimises the possibility of segregation by size during the subsequent production of the composition.

The segregation or separation by size can affect the uniformity of the content or dose of the pharmaceutical composition containing the enteric microcapsules.

Another objective of this invention is the production of a pharmaceutical composition in the form of capsules or powder for suspension with diclofenac or one of the salts thereof in microcapsules as the sole active ingredient or in association with a proton pump inhibitor in pellets, for example, omeprazole.

Another objective of this invention is the transformation of the enteric microcapsules with a homogeneous composition and quick release rate of the active ingredient they contain at 6.8 pH or higher, into microcapsules with prolonged release at said simulated intestinal pH.

The production method of the enteric microcapsules, which is the object of this invention, requires FOUR continuous steps. Each one of them fulfils a specific and necessary function. Diagrammatically, the method for obtaining enteric microcapsules comprises:

Step I (A):

Preparing a water-ethanol solution that contains sodium, potassium or ammonium alginate, adding diclofenac or one of the salts thereof and where the active ingredient was previously completely dissolved in the presence of a surfactant and sodium bicarbonate; under stirring at a temperature below 60° C.

The sodium, potassium or epolamine salts of diclofenac present different water solubility characteristics. Adding ethanol or increasing the mixing temperature specifically determine in each case the total dissolution of the salt. When dissolving the active ingredient it is necessary to prevent if from degrading by operating at the lowest possible temperature.

Step II (B):

Slowly adding the previous solution (Step I) to a solution made up of a water soluble calcium salt (preferably calcium chloride) to produce gelation. This step is necessarily slow to prevent the microcapsules formed from agglomerating or sticking together, the precipitation or partial re-crystallisation of diclofenac or the chosen salt and also its possible degradation. Preferably this step is carried out over 2 to 4 hours, and very preferably over 3 hours. Preferably it is done at a temperature below 60° C.

Step III (C):

Re-suspending the microcapsules obtained and isolated in Step II in an aqueous solution of alginate salt, preferably with a concentration of between 0.05% and 0.1%, and preferably under stirring for 30 to 120 minutes at ambient temperature.

It confers a completely enteric character on the microcapsules obtained in Step II and ensures the non-release of the active ingredient at stomach acid pH.

Surprisingly, it has been observed that when the microcapsules produced, are isolated without prior drying and re-suspended under stirring in a significant volume of a very diluted solution of the alginate salt (0.05%-0.1%) and are kept under stirring at ambient temperature (23-25° C.) for 30 to 120 minutes, all the microcapsules, including the smaller size ones, have enteric behaviour. Preferably the chosen volume for the resuspension is 10 to 20 liters of diluted sodium alginate solution (0.1%) for every kilogram of isolated and wet microcapsules.

Step IV (D):

The microcapsules obtained in Step III isolated and following drying are sieved through meshes of 1000 to 250 micron and the fraction contained between both meshes is specifically selected for producing the chosen pharmaceutical composition, discarding the rest.

This step is unexpectedly a necessary condition in that:
a) it removes the fraction of smaller size microcapsules (below 250 micron) minimising the taste and astringency that are characteristic of diclofenac or the salts thereof, from the mixture of different sized microcapsules that were obtained.

This removal of microcapsules smaller than 250 micron revealed in experiments that it contributes subsequently to producing the pharmaceutical composition by simplifying the masking of the taste and astringency of the active ingredient.

b) it also removes the fraction of larger size microcapsules (over 1000 micron) minimising the possibility of segregation by size.

In experiments it was observed that the presence of particles sized larger than 1000 micron affects the uniformity of the content or the uniformity of the dose of the pharmaceutical composition containing them.

The production method described revealed that the microcapsule content sized at 1000 micron or more fluctuates between 1 and 2%, usually below 2% and the microcapsule content sized at less than 250 micron is approximately 1% of the dry weight of the microcapsules obtained.

The fraction of microcapsules sized between 250 and 1000 micron was revealed to be the most convenient for resolving the said problems of taste or segregation and simplifying the production of the chosen pharmaceutical composition.

Said fraction between 250 and 1000 micron revealed that it is made up of a mixture of variable sized particles.

So for example in different batches it was found that the weight retained by a mesh with an 850 micron opening varied between 20 and 30% of the dry weight of the mixture, the weight retained by the mesh with a 710 micron opening varied between 20 and 30%, the weight retained by a mesh with a 590 micron opening varied between 20 and 40% and the weight retained by a mesh with a 420 micron opening varied between 5 and 24%.

However, unexpectedly, the said variability of the microcapsules size between 250 and 1000 micron does not affect the production of the pharmaceutical composition containing them, it contributes to their better taste and the content uniformity. It was observed that it is essential to discard the microcapsules sized less than 250 micron and larger than 1000 micron The fraction between the 1000 and 250 micron meshes fulfils the objectives mentioned above and is satisfactory for producing the chosen oral pharmaceutical composition.

For the production of microcapsules with enteric properties without the need of the enteric coating aggregate, surprisingly it was found that when the active ingredient (diclofenac or one of the salts thereof) is completely dissolved in a solution and not in suspension, which contains sodium alginate, sodium bicarbonate and a surfactant, and the unit is dispersed by a drop disperser, or pistol over an aqueous solution of calcium chloride and kept under vigorous stirring for up to 3 hours, gelation of the calcium alginate formed occurs, which leads to obtaining the enteric microcapsules containing the originally dissolved active ingredient, which have the above-mentioned characteristics and objectives.

The surfactant is advantageously selected between sorbitan monostearate, sorbitan monooleate (ARLACEL 83), polyoxyethylene sorbitan monostearate; polyoxyethylene sorbitan monooleate; polyoxyethylene sorbitan monolaurate. Preferably it is polyoxyethylene sorbitan monostearate (Polysorbate 60).

Dissolving the active ingredient beforehand is essential to obtaining the microcapsules with the said characteristics. However, the operating conditions for obtaining the solubilisation of the active ingredient depend specifically on the nature of diclofenac or the diclofenac salt in question (sodium, potassium or epolamine).

So, for example, diclofenac potassium and diclofenac epolamine are more soluble in pure water and in the reaction medium including water-ethanol, polysorbate 60, sodium bicarbonate and sodium alginate, than diclofenac sodium or diclofenac acid.

Surprisingly it was found that it is possible to achieve the complete dissolution of the chosen diclofenac salt by introducing some of the following operating conditions into the microcapsule production method in the step prior to gelation with the calcium salt:
a) adding ethanol, preferably no more than 50% of the total volume to increase solubility of the salt. However, also to help eliminate it completely as a residual solvent, during the steps of washing and subsequently drying the microcapsules formed.

b) Increasing the temperature of the premixture formed to no more than 58-60° C. and preferably below 44-46° C. before gelation. So for example:

diclofenac potassium: Surprisingly it revealed complete solubility in only 30 minutes under stirring when added to a water-ethanol mixture (95/5) at a concentration of up to 10%, containing 0.2% polysorbate 60, potassium bicarbonate (6.2%) and sodium alginate (3.90%) and increasing the premixture temperature to 44-46° C.

epolamine diclofenac: In similar operating conditions it determined the complete solubility of the salt immediately.

diclofenac sodium: It required greater water and ethanol content to reach total dissolution at a lower temperature than the mixture prior to gelation with the soluble calcium salt.

It was surprisingly observed that different water-ethanol associations together with the increase in the mixture temperature prior to adding the calcium salt during gelation provides convenient solutions of the diclofenac salts (sodium, potassium, or epolamine) for the simple production of the enteric microcapsules containing said salts and without degrading the active ingredient they contain.

It was analytically shown that:

a) Up to the 60° C. reaction mixture temperature and during the gelation with the calcium salt, the diclofenac was not degraded. No related substances derived from the degradation of diclofenac mentioned in USP were detected in HPSC. However, practical reasons indicate that it is advisable to not go above 55° C.

b) The solubility of the microcapsules formed is relatively low in water-ethanol mixtures. For example, in water/ethanol (90/10) under stirring for 30 minutes at 60° C., solubility was less than 6%. The results unexpectedly indicate that the increase in temperature above the ambient temperature and a certain percentage of ethanol added to the reaction mixture are useful options that can be applied in practise during the production of microcapsules of diclofenac or the respective salts thereof.

Preferably the production method of enteric microcapsules according to the invention is characterized in that the microcapsules contain less than 10%, preferably less than 5%, of diclofenac crystals. Also, preferably the method comprises the following operating sequence:

A) i) preparing a solution of said alginate salt in water (preferably at 95-90%)-ethanol (preferably at 5-10%) at ambient temperature and under stirring;

ii) adding to the previous solution sodium bicarbonate (preferably at 6.20% W/V), polyoxyethylene sorbitan monostearate (Polysorbate 60) (preferably at 0.20% W/V), diclofenac or one of the salts thereof (preferably at 9.90% W/V) and stirring for 2 hours to obtain a solution at a temperature under 60° C.;

B) i) transferring the previous mixture to a first pressurizable stainless steel reactor (REACTOR I);

ii) at the same time, in a second flat-bottomed reactor, with lower sieve plate and metallic mesh No 40, preparing under stirring and at ambient temperature a solution of calcium chloride at a concentration equivalent to or higher than 10% W/V, preferably at 5% W/V (REACTOR II);

iii) transferring under pressure the mixture contained in the first pressurizable reactor (REACTOR I) to the second, flat-bottomed reactor (REACTOR II) via a double jacket stainless steel conduit heated with steam to maintain the temperature of the mixture passing through it, under 58-60° C., so that the solution is added to the gelation medium contained in the second reactor (REACTOR II);

iv) leaving the microcapsules formed in contact for 15 minutes in the reaction medium, separating them by filtering;

C) resuspending them in a solution with a low content of said alginate salt (preferably at 0.1%) under stirring for 30 to 120 minutes at ambient temperature;

D) i) separating the microcapsules by filtering, drying and sieving successively through 1000 and 250 micron meshes;

ii) selecting the fraction of enteric microcapsules sized between 250 and 1000 micron, discarding the microcapsules sized smaller than 250 micron and larger than 1000 micron.

Other preferable embodiments of the method according to the invention are described in the corresponding dependent claims.

Surprisingly it was noted that the microcapsules obtained by the described method have in some cases (potassium diclofenac) an irregular shape, with the spherical shape not prevailing. It is interpreted that the presence of the diclofenac salt in solution in the reaction mixture favours quick gelation when beforehand calcium chloride is added to the solution causing:

a) Greater irregularity in the shape of the microcapsules obtained.

b) Greater contact surface with the medium than equal weight spherical or partially spherical microcapsules.

c) High active ingredient content in the microcapsules—between 55% and 65% of the dry weight of the microcapsules. Significant difference in comparison with the enteric pellets having different active ingredients with much lower content, virtually of the order of just 10%.

d) Low release capacity of diclofenac at pH 1.0 (simulation of gastric pH).

e) High release speed of their content and dissolution at pH 6.8 (simulation of intestinal pH).

f) Presence of amorphous diclofenac in the microcapsules.

g) Low intensity of bitter taste and astringency

Characteristic of the enteric microcapsules and particularly important in practical terms for the production of the pharmaceutical composition that requires prolonged contact with buccal mucus.

Not just because of its bitter taste, also the marked astringency of diclofenac and the salts thereof.

The microcapsules obtained according to this invention have an homogeneous composition, that is, they are formed only by the gelation of sodium alginate with a soluble calcium salt, and fulfil the above-mentioned characteristics (resistance to acid pH, quick release at intestinal pH, absence of astringency or bitter taste, mechanical resistance, physical-chemical stability, etc.), but they also reveal unexpected and surprising biological behaviour.

In the biological assay described in the Experiment Section, the following has been observed with equivalent doses:

a) that the microcapsules have similar anti-inflammatory and analgesic activity to the references;

b) that they cause lesser gastric aggressiveness than the comparison references.

The references used were in equivalent doses: in one case diclofenac potassium pure active ingredient and the other reference was the product Volquick, which contains diclofenac potassium pure active ingredient, sodium bicarbonate and excipients in the form of powder for suspension in water to be administered orally to patients.

The unexpected results obtained through the biological assay show that the microcapsules with an homogeneous composition that are obtained with the method of the invention are particularly interesting for producing the chosen pharmaceutical composition in that they show equivalent activity and less aggressiveness than the active ingredient they contain (diclofenac potassium) when biologically comparing their behaviour with important references, applied therapeutically: such as a) the pure active ingredient and b) diclofenac potassium in association with sodium bicarbonate (Volquick®).

Specifically: the said properties of the enteric microcapsules of the invention and their biological behaviour determine significant flexibility and practical importance for their application in the production of the chosen pharmaceutical composition.

So, for example:
a) It is feasible to use them to prepare an oral pharmaceutical composition of the granulated type for the suspension of single or multiple doses, tablets and chewable tablets (not described to date by third parties for diclofenac or the salts thereof) and whose biological study results will be described in the Experiment Section. It is relevant to highlight that the bitter taste and strong astringency of diclofenac and the salts thereof has, to date, prevented the production of chewable tablets containing said active ingredients, and this invention makes it possible to resolve this easily via the enteric microcapsules obtained. The Experiment Section describes the result of the Clinical Study on chewable tablets produced with the said enteric microcapsules.
b) Thanks to the stability of the enteric microcapsules, it is also feasible to associate them with other active ingredients in a pharmaceutical composition with "dual" activity. A preferred but not limiting association includes associating the microcapsules with proton pump inhibitors in pellets. For immediate protection of the gastric mucus (the microcapsules) and the prolonged anti-acid effect of the inhibitor. With omeprazole, lanzoprazole or esomeprazole pellets being chosen. Such compositions are characterized because by being multiparticled (microgranules and pellets) they pass through the stomach easily (without degrading) and reach the intestine where they are absorbed and can exist in various formats. Such as, for example: capsules, tablets, chewable tablets, single dose powder for suspension or multiple dose suspensions that are prepared immediately prior to use.

The Experiment Section also describes the biological assay that enabled revealing satisfactory therapeutic levels of diclofenac and omeprazole after administering to patients capsules containing microcapsules of diclofenac sodium and omeprazole pellets.

Among the proton pump inhibitors, omeprazole is highlighted as one of the most important anti-ulcer agents currently used in clinical applications. It is absorbed by the intestine and significantly inhibits the gastric secretion of hydrochloric acid. So, for example, administering 20 mg maintains the gastric pH at 4 or above for 14 to 17 hours.

Generally, pellets are used that contain only 8 to 10% omeprazole in the form of the pure active ingredient and the remaining components are intended to ensure stability in the gastric acid medium. The dosage is extensive and is associated with the patient's particular pathology. The literature highlights, according to particular cases, unit doses for therapeutic application containing 5, 10, 20 and 40 mg of omeprazole.

The unit doses also has various options for other proton pump inhibitors. For example, for lanzoprazole between 15 and 30 mg, for esomeprazole between 10 and 40 mg, and for pantoprazole between 20 and 40.

As for diclofenac and the salts thereof, the variability of the content of commercial pharmaceutical compositions is extensive. So, for example, there are formulas containing 25, 50 or 75 mg per gastro-resistant, quick release capsule. Other capsules contain 100 mg of sodium diclofenac, of which a fraction is released immediately and the rest with a prolonged release.

This invention is also aimed at an oral multiparticled pharmaceutical composition in the form of capsules, powder for suspension and water, or chewable tablets, CHARACTERIZED in that it comprises 25 to 100 mg of diclofenac or one of the salts thereof, sodium, potassium or epolamine, in the form of enteric microcapsules produced using a method according to the invention. Preferably the microcapsules do not release more than 2% of diclofenac or one of the salts thereof and preferably less than 1% in an acidic medium (preferably HCl 0.1 N) over 2 hours under stirring (preferably 50 rpm or 75 rpm) and release at least 90% of the active ingredient they contain over 30 minutes at pH 6.8 or higher, also under stirring. Other preferable compositions are described in the corresponding dependent claims.

The prolonged release microcapsules are prepared from quick release enteric microcapsules by virtue of coating said microcapsules in spray using model MFL.01 vector equipment (Vector Micro Fluid Bed Dryer, model MFL.01) with a suspension of ethanol (95-90%-water (5-10%) that contains 0.5 to 1.0% of triethyl acetate; 1.2 to 1.8% of talc and 5.0 to 7.0% of type B ammonium methacrylate copolymer (Eudragit® RS). Thus, the invention is also aimed at a method of producing prolonged release microcapsules of diclofenac or one of the salts thereof CHARACTERIZED in that it comprises:

a) coating the enteric microcapsules with homogeneous composition obtained with a method according to the invention, with a suspension of water-ethanol (preferably in the ratio of 95/5) which contains 0.5% to 1% of triethyl acetate, preferably 1% of triethyl acetate, between 1.2% and 1.8% of talc, preferably 1.6% of talc, and between 5.0% and 7.0% of type B ammonium methacrylate copolymer, preferably 6.3% of type B ammonium methacrylate copolymer, using spray;
b) maintaining the microcapsules in contact with the suspension, preferably over 2 hours, preserving the temperature of the microcapsules due to be coated, at 25 to 30° C. throughout the operation; and
c) separating the coated microcapsules and drying in a kiln under an air current, preferably over 24 hours at a temperature below 40° C.

The invention is also aimed at multiparticled pharmaceutical compositions comprising prolonged release enteric microcapsules obtained by means of a method according to the invention, as described in the corresponding claims.

This invention also enables resolving a therapeutic void by associating in one and the same pharmaceutical composition the therapeutic activity of diclofenac or the salts thereof without aggressiveness on the gastric mucus thanks to the microencapsulation of the active ingredient and the protection of the gastric mucus provided by the proton pump inhibitors with their ability to favourably modify the stomach pH.

The microcapsules of diclofenac or the salts thereof enable producing the chosen multiparticled composition containing diclofenac or one of the salts thereof with the proton pump inhibitor in enteric pellets, also the chosen type, in a simple form on an industrial scale.

Enteric microcapsules, in this invention are, as mentioned, widely applied to produce multiparticled compositions under various pharmaceutical presentation formats.

These include, inter alia:

A) Oral gelatine capsules constitute a conventional way of associating diclofenac or one of the salts thereof and proton pump inhibitor in the form of a multiparticled composition. In a non-limiting way, a chosen composition contains 75 mg of diclofenac sodium microcapsules and 10 mg of omeprazole in pellets in Coni Snap type capsules or the like. This composition is particularly indicated for a dosage of two daily doses. Another convenient composition in capsules for a dosage of three daily doses comprises 50 mg of diclofenac in non-coated microcapsules with 10 mg of omeprazole in pellets.

B) Another multiparticled composition comprises powder for suspension in single dose sachets containing diclofenac sodium non-coated microcapsules with omeprazole pellets together with previously dried sodium alginate as suspension agent and mucus protector, together with other accepted and commonly used pharmaceutical excipients.

The composition is available in single dose sachets of aluminium or other anti-humidity material that preserves the sachet content.

The powder for suspension in the format prior to ingestion is suspended by pouring the content of one sachet into water, and gently stirring.

The preferred content comprises 75 mg of non-coated microencapsulated diclofenac sodium and 10 mg of omeprazole pellets for a dosage of two daily doses and 50 mg of non-coated microencapsulated diclofenac and 10 mg of omeprazole pellets for a dosage of three daily doses.

The composition is particularly useful in old-aged patients or patients who have difficulty in swallowing and prefer to take a pleasant tasting suspension than a capsule.

The composition can also be available in multiple unit doses that can be easily fractioned for the patient.

C) Another multiparticled composition in capsules or powder for suspension comprises diclofenac potassium microcapsules and omeprazole pellets as proton pump inhibitor, and their content in active ingredients was similar to those indicated above in A and B.

D) Another multiparticled composition in capsules or powder for suspension comprises microcapsules of epolamine diclofenac and omeprazole pellets. They were prepared in a similar way to A and B replacing the anti-inflammatory element with diclofenac epolamine.

E) Using the same technology new compositions were prepared containing other proton pump inhibitors in pellets like esomeprazole, lanzoprazole or pantoprazole associated with diclofenac sodium, potassium or epolamine in microcapsules.

F) Multiparticled compositions according to the above description wherein the microcapsules of diclofenac or one of the salts thereof are of the prolonged release type.

In a non-limiting manner, the examples illustrate how this invention is implemented practically.

EXAMPLES

Example I

Preparing Enteric Microcapsules of Calcium Alginate Containing Diclofenac Potassium Released at pH 6.8 or Above A) i) In a stainless steel reactor with stirring blades, 38.0 liters of deionised water, 2.0 liters of ethanol and 1.560 kg of sodium alginate were added successively and stirred for 60 minutes at 2000 rpm.
ii) To the above solution polysorbate 60 (0.080 kg.), potassium bicarbonate (2.480 kg) and diclofenac potassium (3.960 kg) were successively added and heated to 58 to 60° C. under stirring at 3000 rpm for 2 hours to obtain a solution.

B) i) The previous solution was transferred to a pressurizable stainless steel container.
ii) At the same time, in a flat-bottomed stainless steel tank, with a sieve plate in the bottom part thereof covered with a No. 40 metallic mesh and stirring blade (600-1500 rpm) 120 liters of deionised water and 6 kg of calcium chloride (5% W/V (weight/volume)) were added and dissolved by stirring for 20 minutes.
iii) The solution with diclofenac potassium and other substances contained in the pressurizable tank was added to the calcium chloride solution contained in the reactor with the sieve plate under the following conditions:
  1) The elements were added under pressure (2.1 kg).
  2) By passing steam through the jacket of the stainless steel transfer conduit, the solution was heated to 58-60° C.
  3) The solution of diclofenac potassium obtained was passed through a system made up of two 0.8 mm diameter peak ends and a disperser with high rotation speed, and was added at the end in the form of small drops in the gelation medium.
  4) The elements were added slowly (3 hours).
iv) Once the addition was complete, the microcapsules & timed were left in contact with the solution of calcium chloride for 15 minutes, it was filtered in the same reactor and washed 2 times with water via resuspension.

C) The isolated microcapsules that do not require prior drying, were resuspended in 120 liters of a sodium alginate solution at 0.1% under stirring for 30 minutes.

D) i) Following filtration, the microcapsules obtained were dried in a fluid bed, sieved, and
ii) the fraction of microcapsules between 250 and 1000 micron meshes was selected for producing the chosen pharmaceutical composition. Only 2% were found above 1000, and only 1% under 250 micron. Both fractions were discarded.

E) The fraction of microcapsules obtained and selected (3.500 kg) showed:
  a) Content: 63 mg of diclofenac potassium/100 mg of microcapsules–Humidity: 7.3%.

b) Dissolution:
1) A simulated stomach pH (HCl 0.1 N) for 2 hours and under stirring (50 rpm or 75 rpm) does not release a significant amount of diclofenac.
2) After 2 hours with an acidic pH, the pH was changed, taking the microcapsules to a simulated duodenal pH (phosphate buffer pH 6.8). Under stirring and taking samples after 15, 30 and 45 minutes, after changing the pH the percentage of diclofenac potassium dissolved was respectively: 72.7% (after 15 minutes), 92.8% (after 30 minutes) and 97.9% (after 45 minutes).
c) Format: In the microcapsules obtained, the irregular shaped prevailed over the spherical shape.
d) Taste: very little unpleasant taste and astringency typical of diclofenac potassium.
Taste Assay:
A panel made up of 8 healthy volunteers compared the taste of two samples from the described production method. The samples were as follows:
A) microcapsules produced and isolated according to step C) of the method, but previously vacuum dried.
B) microcapsules produced according to the method, dried and sieved and selecting the fraction of microcapsules between 250 and 1000 micron meshes, according to step D).
Panel conclusion: It was confirmed that the A type microcapsules preserve the characteristic taste and astringency of the diclofenac that they contain, whereas the type B microcapsules have very little unpleasant taste and astringency.
It was determined that the difference in taste between both samples was significant.

e) In the microcapsules obtained no degradation products were found, or related substances due to applying the analytical method described in USP.
f) Using X-ray spectroscopy no signs corresponding to diclofenac potassium crystals were observed in the enteric microcapsules obtained.

Experimental Pharmacological Study:
A) Anti-Inflammatory Activity and Gastric Aggressiveness A comparison was made, in equivalent doses, of the anti-inflammatory activity and gastric aggressiveness of the microcapsules obtained, with 2 references: a. diclofenac potassium pure active ingredient and b. Voltquick, powder for preparing an oral solution containing diclofenac potassium and sodium bicarbonate.

Adult Sprague Dawley rats, of both sexes, were used.

To determine the anti-inflammatory activity, a Carrageenin-induced edema in the paw was used, according to the method of Winter, Risley and Nuss (Method. "Proc. Soc. Exp. Biol. Med" 11, 544; 1962). The Pisanti-Volterra method, (Il Farmaco, de. Pr. 25 (2). 105-121: 1970) was used to determined the gastric tolerance. The equivalent doses assessed, coinciding with the doses used in the effectiveness test, were 12.5, 25.0, and 50.0 mg/kg. The following scores were attributed according to the type and intensity of the injury observed:

Score 0=Normal stomach without injury; 1=Haemorrhaging points; 2=Haemorrhaging diffusion (reddening of the surface); 3=1-5 small ulcers (<3 mm); 4=Large number of small ulcers or a deep isolated ulceration; 5=Many ulcers of various size; 6=Perforated ulcer.

The degree of gastric injury is defined by the average score; the higher score corresponds to a greater gastric injury

TABLE # 1

| Dose: 12.5 mg/kg | % Inflammation inhibition | | | | | Degree of Gastric Injury |
|---|---|---|---|---|---|---|
| | $1^{st}$ hour | $2^{nd}$ hour | $3^{rd}$ hour | $4^{th}$ hour | 5th hour | Avg. score ± e.s. |
| Microencapsulated diclofenac potassium | 45.3 ± 10.1 | 36.8 ± 7.32 | 32.8 ± 6.5 | 30.3 ± 5.9 | 23-6 ± 6.3 | 0.86 ± 0.24 |
| Voltquick | 31.1 ± 12.7 | 32.1 ± 9.1 | 29.4 ± 6.3 | 30.7 ± 5.4 | 14.7 ± 4.3 | 2.60 ± 0.22 |
| diclofenac potassium pure active ingredient | 37.2 ± 12.2 | 42.5 ± 13.1 | 28.3 ± 9.5 | 30.6 ± 9.8 | 29.7 ± 10.8 | 2.64 ± 0.59 |

TABLE # 2

| Dose: 25.0 mg/kg | % Inflammation inhibition | | | | | Degree of Gastric Injury |
|---|---|---|---|---|---|---|
| | $1^{st}$ hour | $2^{nd}$ hour | $3^{rd}$ hour | $4^{th}$ hour | 5th hour | Avg. score ± e.s. |
| Microencapsulated diclofenac potassium | 46.4 ± 10.6 | 40.7 ± 7.4 | 45.6 ± 4.3 | 36.4 ± 5.3 | 30.4 ± 6.2 | 1.67 ± 0.42 |
| Voltquick | 37.5 ± 11.4 | 43.4 ± 9.2 | 48.5 ± 7.0 | 41.4 ± 9.1 | 28.3 ± 6.3 | 3.60 ± 0.34 |
| diclofenac potassium pure active ingredient | 44.3 ± 13.06 | 36.4 ± 8.49 | 28.0 ± 13.56 | 23.3 ± 6.66 | 15.7 ± 5.61 | 3.81 ± 0.35 |

TABLE # 3

|  | % Inflammation inhibition | | | | | Degree of Gastric Injury |
|---|---|---|---|---|---|---|
| Dose: 50.0 mg/kg | 1st hour | 2nd hour | 3rd hour | 4th hour | 5th hour | Avg Score ± e.s. |
| Microencapsulated diclofenac potassium | 50.0 ± 5.8 | 49.8 ± 4.7 | 48.0 ± 5.9 | 48.3 ± 3.4 | 44.1 ± 3.6 | 3.60 ± 0.38 |
| Voltquick | 30.0 ± 10.2 | 40.9 ± 5.6 | 40.7 ± 6.9 | 46.7 ± 6.2 | 50.0 ± 7.7 | 4.30 ± 0.26 |
| diclofenac potassium pure active ingredient | 41.3 ± 14.7 | 45.8 ± 8.3 | 41.4 ± 6.9 | 47.2 ± 5.2 | 43.2 ± 4.5 | 4.80 ± 0.50 |

The results indicate that the enteric microcapsules have equal anti-inflammatory activity and less aggressiveness on the gastric mucus, in comparison with the references used.

The method described was applied to other diclofenac salts (sodium and epolamine).

B) Anakesic Activity

Adult male Swiss rats were used in the assay, 28-30 g in weight, 10 animals per treatment group or for each assessed dose level.

1—The analgesic activity/action was assessed by using an acute chemical visceral pain model, the abdominal contraction test with acetic acid (Writhing Test) (Miranda, H; Puig, M; Prieto, J. C.; Pinardi, G. Synergism between paracetamol and nonsteroidal anti-inflammatory drugs in experimental acute pain. Pain (12) 2006. 22-28) (Hayashi, G. Takemori, A. E. The Type of Analgesic-Receptor interaction involved in certain analgesic assays. European Journal of Pharmacology 16 (1971) 63-66. North Holland Publishing Company)

The rats were treated with microencapsulated diclofenac potassium, Voltquick, and diclofenac potassium, pure active ingredient, in doses of 12.5 and 25 mg/Kg.

The antinociceptive activity was expressed as the inhibition percentage of the number of contractions observed in the animals in the groups treated at each of the assessed dose levels, with respect to the number of contractions in the study control animals.

The results obtained are detailed in Table 1 and 2.

TABLE # 1

| Dose: 12.5 mg/kg | Analgesic Activity (% Inhibition) Avg. Score ± e.s. |
|---|---|
| Microencapsulated diclofenac potassium | 54.16 ± 3.99 |
| Voltquick | 51.82 ± 4.68 |
| diclofenac potassium pure active ingredient | 53.23 ± 5.53 |

TABLE # 2

| Dose: 25.0 mg/kg | Analgesic Activity (% Inhibition) Avg. Score ± e.s. |
|---|---|
| Microencapsulated diclofenac potassium | 68.66 ± 4.13 |
| Voltquick | 66.32 ± 3.40 |
| diclofenac potassium pure active ingredient | 67.26 ± 4.62 |

The 3 assessed components did not show any significant differences in their analgesic action with the methodology used, in the established doses.

Surprisingly the biological assays showed a) similar anti-inflammatory activity b) similar analgesic activity c) lower aggressiveness of the enteric microcapsules containing diclofenac potassium and produced with the method of this invention, than the references used as points of comparison.

Example II

Preparing Enteric Alginate Microcapsules Containing Diclofenac Potassium Released at pH 6.8 or Above Enteric microcapsules released at pH 6.8 or higher containing diclofenac potassium were produced according to the method described in EXAMPLE I with the following modifications:

a) The water-ethanol mixture (95/5%) containing sodium alginate was replaced with a water-ethanol (90/10) solution and sodium alginate.

b) It was heated to 44-46° C. under stirring until a solution was obtained from the suspension containing sodium alginate, polysorbate 60, potassium bicarbonate, and diclofenac potassium, which was added slowly and maintaining the temperature throughout the whole gelation reaction with the calcium chloride solution.

The greater percentage of ethanol contributed to dissolving the diclofenac potassium in the mixture made up of sodium alginate, polysorbate 60 and sodium bicarbonate and enabled continuing the method at a temperature of 44-46° C.

Example III

Preparing Enteric Alginate Microcapsules Containing Diclofenac Potassium and which are Released at pH 6.8 or Higher Enteric diclofenac potassium microcapsules were produced according to the method described in EXAMPLE I with the following modifications:

a) The water-ethanol (95/5%) mixture containing sodium alginate was replaced with a water-ethanol (50/50) solution containing sodium alginate b) It was heated to 28-30° C. under stirring until a solution was obtained from the suspension containing sodium alginate, polysorbate 60, potassium bicarbonate and diclofenac potassium, which was added slowly and maintaining the temperature throughout the whole gelation reaction with the calcium chloride solution.

The complete dissolution of the mixture components in ethanol-water (50/50) made it possible to carry out the method at a lower temperature (28-30° C.).

Example IV

Preparing Enteric Alginate Microcapsules Containing Diclofenac Sodium Released at pH 6.8 or Higher a) In a stainless steel reactor with blade stirring (2000 r.p.m.) deionised water (19 liters) and ethanol (1 liter) were added successively, heated to 44-46° C. and, under stirring, polysorbate 60 (0.02 kg) and sodium alginate (0.39 kg) were added. Stirring was maintained until complete dissolution.
b) To the above solution, under stirring and maintaining the temperature (44-46° C.), sodium bicarbonate (0.62 kg) and diclofenac sodium (0.94 kg) were added. It was stirred for approximately 1 hour until complete dissolution.
c) The above solution was transferred to a pressurizable stainless steel tank.
d) At the same time, in a flat-bottomed stainless steel tank, with a sieve plate in the bottom part thereof covered with a No. 40 mesh and blade stirring, 120 liter of water and 1.50 kg of calcium chloride were added, and it was dissolved under stirring.
e) The solution of diclofenac sodium and other substances contained in the pressurizable tank was added to the calcium chloride solution contained in the reactor with the sieve plate under the following operating conditions:
  1) The elements were added under pressure (1 kg).
  2) The temperature was maintained at 44-46° C. throughout the whole addition process.
  3) The solution of sodium alginate, polysorbate 60, sodium bicarbonate and diclofenac sodium was passed through a system made up of two 0.8 diameter peak ends and a disperser with a high rotation speed, for adding this solution, in the form of small drops, to the gelation medium.
  4) The elements were added slowly (1.5 hours).
f) After the addition, the microcapsules were left in contact with the solution for 15 minutes, filtered in the same sieved reactor and washed 2 times with deionised water via resuspension.
g) The isolated microcapsules, without any previously drying, were resuspended in a solution of sodium alginate at 0.1% under stirring for 30 minutes.
h) Following separation by filtration, they were dried in a fluid bed kiln and sieved successively through 250 and 1000 micron meshes. The chosen fraction was between the two meshes.

The dry microcapsules were sieved and the fraction between meshes 250 and 1000 was selected for producing the chosen pharmaceutical composition.

The fraction of microcapsules obtained and selected (3.600 kg.) revealed:
a) content: 58.2 mg of diclofenac sodium for every 100 mg of microcapsules. Humidity: 8.4% (63% in dry microcapsules)
b) Dissolution:
  1) With a simulated intestinal pH (HCL 0.1 N) for 2 hours and under stirring (50 rpm), the release of diclofenac sodium was low (1.18%).
  2) After 2 hours with an acidic pH, the pH was changed, taking the microcapsules to a simulated duodenal pH (phosphate buffer pH 6.8). Under stirring at 50 rpm samples were taken after 5, 15, 30 and 45 minutes, once the pH had been changed.

The percentage of diclofenac sodium dissolved was respectively 26.44% after 5 minutes, 52.66% (after 15 minutes), 72.44% after 30 minutes and 82.96% after 45 minutes.
c) Taste: very little of the characteristic unpleasant taste and astringency of diclofenac sodium was observed.

Example V

Preparing Enteric Alginate Microcapsules Containing Diclofenac Epolamine Released at pH 6.8 or Higher Enteric microcapsules of diclofenac epolamine were produced according to EXAMPLE I, with the following modifications:
a) The mixture made up of 95% water, 5% ethanol and sodium alginate mentioned in EXAMPLE I was replaced with 90% water, 10% ethanol and sodium alginate, and
b) It was heated to 44-46° C. and stirred until a solution was obtained from the suspension containing sodium alginate, polysorbate 60, sodium bicarbonate and diclofenac epolamine, which was added slowly and maintaining the temperature throughout the gelation reaction with the calcium chloride solution.

The enteric microcapsules obtained revealed:
a) content was 53.9 mg. of diclofenac epolamine for every 100 mg. of microcapsules with a humidity of 7.9% (58.1% on dry microcapsules).
b) Resistance to acidic pH and release of diclofenac epolamine at pH higher than 6.8.
c) Taste: absence of the unpleasant taste and astringency.

Example VI

Preparing Oral Multiparticled Capsules Containing 75 mg of Diclofenac Sodium in Enteric Microcapsules and 10 mg of Omeprazole Pellets They were prepared by adding to an automatic machine, per capsule, the equivalent to 75 mg of diclofenac sodium in the form of enteric microcapsules of diclofenac sodium and 10 mg of omeprazole in the form of pellets.

Coni Snap type capsules were used.

For both active ingredients, the said amounts were corrected by weight and according to the content determined previously for the microcapsules or pellets.

The capsules were conditioned in orientated type polyamide blister O.P.A 25-PVC 60/aluminium.
a) Experiment pharmacological study The mixture formed by the equivalent to 75 mg of diclofenac potassium in the form of microcapsules and 10 mg of omeprazole in the form of pellets with which the said capsules are produced, was pharmacologically assessed to determine the greater gastric tolerance that determines the presence of the proton pump inhibitor.

The assessment was carried out on adult Dawley rats, of both sexes.

The Pisanti-Volterra model was used, continuing the study mentioned in Example I, but in the presence of the proton pump inhibitor.

The terms of comparison were a) diclofenac potassium pure active ingredient b) diclofenac potassium in the form of microcapsules made according to Example I, c) diclofenac potassium and sodium bicarbonate in powder for preparing an oral solution (Volquick sachets).

Increasing doses of the mixture and the references were administered, expressed by the content of diclofenac potassium and including doses of diclofenac higher than therapeutic doses.

When repeated doses are administered, the protection provided by the association increases, in comparison with the irritant gastric effect of the anti-inflammatory on its own.

The result indicated that the ulcerogenic effect of the mixture containing diclofenac potassium on the gastric mucus of rats was marked or totally deleted (according to the doses administered). In the mixture made up of diclofenac potassium (75 mg.) and omeprazole pellets (10 mg.) the significant difference and greater ulcerogenic effect was also observed in the three terms of comparison mentioned b) Pharmacokinetic study of the capsules containing the association: diclofenac 75 mg and omeprazole 10 mg Objectives: To determine in 18 healthy volunteers the plasmatic levels of diclofenac and omeprazole that are reached after a single administration of: 1 capsule containing 10 mg of omeprazole in pellets with enteric release and 75 mg of microencapsulated gastro-resistant diclofenac prepared according to this invention.

Material and methods: A total of 18 healthy volunteers were selected according to standard practice, of both sexes, and aged between 21 and 50 years old, who did not take any medicine in the 15 days prior to the study and had nil by mouth for at least 8 hours, prior to the medicine being administered. The subjects took a capsule containing 10 mg of omeprazole with a gastro-resistant coating and 75 mg of microencapsulated diclofenac, with 200 ml of water. Then, 11 blood samples were taken, each 10 ml, throughout the 9 hours of assessment, one basal sample and then 10 of the administration from the capsule, after 10; 20; 30; 60; 90; 120; 150; 180; 360 and 540 minutes.

The subjects did not swallow liquids or food for at least 2 hours after administering the tablet in the study. A standardised diet was offered during the course of the study. After administering the formula with diclofenac and omeprazole, the participants remained in the medical centre for 10 hours.

Technique for Determining Diclofenac-Omeprazole in Serum Samples

To simultaneously determine diclofenac-omeprazole, by HPLC, the serum was extracted with dichloromethane using a liquid to liquid separation method. The internal standard was phenobarbital. It was monitored with a UV detector, at a wave length of 215 nm, and at a temperature of 40° C. Also a 5 um Nucleodur Gravity C8 250/4 column was used.

Quantification limits: diclofenac: 20 ng/ml, omeprazole: 5 ng/ml

Results:

For diclofenac (all the values are expressed as average+/−standard deviation):

Area Under the Curve, concentration according to time (ng/ml/h):$ABC_{0-30}$: 11.06±13.49; $ABC_{0-60}$: 89.49±84.99; $ABC_{0-150}$: 686.96±370.89; $ABC_{0-180}$: 884.53±403.96; $ABC_{0-360}$: 1470.53±571.03; $ABC_{0-540}$: 1599.70±615.27. C Max (en ng/ml): 621.83±261.10. T Max (hours): 2.11±0.63.

For Omeprazole (all the values are expressed as average+/−standard deviation):

Area Under the Curve, concentration according to time (ng/ml/h), expressed as average+/−standard deviation (DE): $ABC_{0-30}$ 1.80±2.42; $ABC_{0-60}$: 22.80±24.28; $ABC_{0-150}$: 125.15±81.16; $ABC_{0-180}$: 139.41±95.34; $ABC_{0-360}$: 180.28±162.35; $ABC_{0-540}$: 186.49±176.28. C Max (ng/ml): 126.91±87.58. T Max (hours): 1.40±0.45.

Conclusions: The results of the pharmacokinetic study carried out, provide plasmatic values within the expected ranges, according to the bibliography, for the single dose of diclofenac 75+omeprazole 10 mg.

| Plasmatic Concentration of diclofenac in ng/mL | | | | | | | | | | | | | | | | | | |
|---|---|---|---|---|---|---|---|---|---|---|---|---|---|---|---|---|---|---|
| minut | VO | VOL. 2 | VOL. 3 | VOL. 4 | VOL. 5 | VOL. 6 | VOL. 7 | VOL. 8 | VOL. 9 | VOL. 10 | VOL. 11 | VOL. 12 | VOL. 13 | VOL. 14 | VOL. 15 | VOL. 16 | VOL. 17 | VOL. 18 |
| 0 | 0 | 0 | 0 | 0 | 0 | 0 | 0 | 0 | 0 | 0 | 0 | 0 | 0 | 0 | 0 | 0 | 0 | 0 |
| 10 | 0 | 0 | 0 | 0 | 0 | 10 | 0 | 0 | 0 | 29 | 0 | 0 | 26 | 0 | 0 | 0 | 0 | 0 |
| 20 | 0 | 0 | 0 | 56 | 82 | 81 | 10 | 0 | 99 | 45 | 0 | 22 | 35 | 0 | 0 | 0 | 0 | 0 |
| 30 | 0 | 0 | 175 | 136 | 288 | 275 | 23 | 57 | 106 | 150 | 12 | 33 | 131 | 0 | 0 | 8 | 0 | 7 |
| 60 | 0 | 38 | 521 | 613 | 435 | 513 | 303 | 112 | 270 | 395 | 28 | 56 | 297 | 64 | 0 | 520 | 46 | 35 |
| 90 | 72 | 94 | 776 | 745 | 511 | 499 | 276 | 204 | 341 | 524 | 54 | 301 | 531 | 353 | 94 | 741 | 611 | 471 |
| 120 | 201 | 301 | 964 | 655 | 411 | 475 | 264 | 331 | 298 | 242 | 141 | 280 | 460 | 316 | 252 | 796 | 1266 | 317 |
| 150 | 389 | 886 | 1156 | 632 | 335 | 394 | 426 | 531 | 294 | 201 | 358 | 356 | 286 | 417 | 415 | 585 | 548 | 224 |
| 180 | 641 | 784 | 556 | 37 | 195 | 173 | 432 | 433 | 154 | 139 | 283 | 659 | 213 | 243 | 77 | 326 | 316 | 129 |
| 360 | 106 | 52 | 135 | 29 | 84 | 54 | 120 | 29 | 33 | 49 | 34 | 142 | 49 | 41 | 49 | 146 | 42 | 48 |
| 540 | 20 | 12 | 32 | 9 | 19 | 8 | 51 | 6 | 6 | 23 | 11 | 35 | 0 | 10 | 39 | 0 | 5 | 24 |

| Plasmatic concentration of omeprazole in ng/ml | | | | | | | | | | | | | | | | | | |
|---|---|---|---|---|---|---|---|---|---|---|---|---|---|---|---|---|---|---|
| minut | VO | VOL. 2 | VOL. 3 | VOL. 4 | VOL. 5 | VOL. 6 | VOL. 7 | VOL. 8 | VOL. 9 | VOL. 10 | VOL. 11 | VOL. 12 | VOL. 13 | VOL 14 | VOL. 15 | VOL. 16 | VOL. 17 | VOL. 18 |
| 0 | 0 | 0 | 0 | 0 | 0 | 0 | 0 | 0 | 0 | 0 | 0 | 0 | 0 | 0 | 0 | 0 | 0 | 0 |
| 10 | 0 | 0 | 0 | 0 | 0 | 0 | 0 | 0 | 0 | 6 | 0 | 0 | 5 | 0 | 0 | 0 | 0 | 0 |
| 20 | 0 | 0 | 0 | 6 | 15 | 11 | 7 | 0 | 0 | 7 | 11 | 0 | 0 | 10 | 0 | 0 | 0 | 0 |
| 30 | 0 | 0 | 0 | 19 | 53 | 25 | 23 | 8 | 5 | 14 | 18 | 1 | 0 | 58 | 0 | 0 | 6 | 0 | 6 |
| 60 | 0 | 0 | 29 | 124 | 88 | 140 | 23 | 62 | 25 | 135 | 50 | 58 | 12 | 71 | 71 | 0 | 378 | 0 | 12 |
| 90 | 0 | 57 | 80 | 65 | 39 | 56 | 12 | 122 | 28 | 96 | 27 | 72 | 133 | 34 | 268 | 71 | 202 | 62 | 139 |
| 120 | 0 | 70 | 149 | 34 | 19 | 50 | 9 | 51 | 32 | 43 | 15 | 42 | 74 | 16 | 54 | 77 | 165 | 213 | 64 |

-continued

| | | | | | | | | Plasmatic concentration of omeprazole in ng/ml | | | | | | | | | | |
|---|---|---|---|---|---|---|---|---|---|---|---|---|---|---|---|---|---|---|
| minut | VO | VOL. 2 | VOL. 3 | VOL. 4 | VOL. 5 | VOL. 6 | VOL. 7 | VOL. 8 | VOL. 9 | VOL. 10 | VOL. 11 | VOL. 12 | VOL. 13 | VOL 14 | VOL. 15 | VOL. 16 | VOL. 17 | VOL. 18 |
| 150 | 30 | 122 | 22 | 11 | 17 | 6 | 17 | 16 | 19 | 9 | 16 | 43 | 9 | 21 | 43 | 102 | 87 | 23 |
| 180 | 16 | 63 | 10 | 0 | 10 | 6 | 6 | 7 | 9 | 5 | 9 | 31 | 6 | 15 | 9 | 159 | 50 | 6 |
| 360 | 10 | 9 | 0 | 0 | 0 | 0 | 0 | 5 | 0 | 0 | 0 | 0 | 0 | 0 | 7 | 44 | 0 | 0 |
| 540 | 0 | 0 | 0 | 0 | 0 | 0 | 0 | 0 | 0 | 0 | 0 | 0 | 0 | 0 | 0 | 0 | 0 | 0 |

Example VII

Preparing Oral Multiparticled Capsules Containing 50 mg of Diclofenac Sodium in Enteric Microcapsules and 10 mg of Omeprazole Pellets They were prepared according to the method described in EXAMPLE VI, but adding, in each capsule, the equivalent to 50 mg of diclofenac sodium in the than of enteric immediate release diclofenac sodium and 10 mg omeprazole in the form of pellets. Both corrected by title.

Example VIII

Preparing Powder for Oral Suspension Containing 75 mg of Diclofenac Potassium in Enteric Microcapsules and 10 mg of Omeprazole Pellets 1000 units were prepared using equipment with two filling steps to meter the active ingredients, omeprazole pellets and microencapsulated enteric diclofenac potassium, prepared with the process of this invention in a prior mixture made up of excipients commonly used in pharmaceutics (Manitol powder, dry corn starch, Primojel, Aerosil 200, Avicel Cl 661), appetisers (Durarome Apple, Durarome Lemon) and sweeteners (sucralose and sugar in sufficient amount for a final weight of 2000 mg per unit dose. The sachets were of the triple folia type.

Example IX

Preparing Powder for Oral Suspension Containing 10 mg of Omeprazole Pellets and 50 mg of Diclofenac Potassium in Enteric Microcapsules Prepared with the Process of this Invention They were prepared according to EXAMPLE VIII.

Example X

Preparing Powder for Oral Suspension Containing 75 mg of Diclofenac Sodium in Enteric Microcapsules and 10 mg of Omeprazole Pellets They were prepared according to EXAMPLE VIII.

Example XI

Preparing Powder for Oral Suspension Containing 50 mg of Diclofenac Sodium in Enteric Microcapsules and 10 mg of Omeprazole Pellets They were prepared according to EXAMPLE IX.

Example XII

Preparing Capsules Made Only with the Described Microcapsules of Diclofenac or One of the Salts Thereof, Containing Optionally Between 25 and 100 mg of Active Ingredient They were produced as indicated in EXAMPLE VI.

Example XIII

Preparing Powder for Oral Suspension with Enteric Microcapsules of Diclofenac or One of the Salts Thereof Four pharmaceutical compositions containing 2000 units of power for suspension were prepared in a similar way, with each composition containing in sachets the equivalent to 25, 50, 75 and 100 mg of diclofenac potassium pure active ingredient in the form of enteric microcapsules of diclofenac potassium produced with the method of this invention following mixture of the microcapsules in an atmosphere with low humidity with excipients used commonly in pharmacy (Manitol powder, dry corn starch, Primojel, Aerosil 200 Avicel C I 661) appetising agents (Durarome Apple, Durarome Lemon) and sweeteners (sucralose) and sugar in sufficient quantity for a final weight of 2000 mg per unit dose. The sachets used were the triple folia type.

Using the same method pharmaceutical compositions were prepared in the form of powder for suspension in sachets with microcapsules of diclofenac sodium and microcapsules of diclofenac epolamine produced according to the method of this invention with a content per unit dose equivalent to 25, 50, 75 and 100 mg of pure active ingredient in each case.

The suspension in water, prior to administration revealed a pleasant taste, without any lumps or the formation of any undesirable precipitate.

Example XIV

Preparing Multiparticled Chewable Tablets with the Described Microcapsules Containing 75 mg of Diclofenac Sodium, Pure Active Ingredient They were produced according to the following sequence of operations.
Step 1)
Pass through 1000 micron sieve and add to a suitable mixer:
 diclofenac sodium 150 grams (in the form of microencapsulated diclofenac sodium prepared with the method of this invention, and corrected by title. Considering that 1 gram of microencapsulated is equivalent to approximately 0.590 grams of diclofenac sodium) together with 175.24 grams of Manitol and granular.

Step 2)

Mix for 15 minutes

Step 3)

Pass through 1000 micron sieve and add to suitable mixer:
180 grams of microcrystalline cellulose (Avicel PH 200), 120 grams of microcrystalline cellulose (Avicel CE 15), 45 grams of carboxymethyl starch (Primojel), 11.26 grams of colloidal silicon anhydride (Aerosil 200) and 48 grams of fumaric acid.

Step 4)

Mix for 30 minutes.

Step 5)

Add to the mixture obtained in Step 4 the one obtained in Step 2 and mix for 30 minutes Step 6)

Pass through 1000 micron sieve and add to mixer:
4.50 grams of sucralose, 6.00 grams of magnesium stearate and 10.0 grams of Durarome Grape Essence.

Step 7)

Mix for 5 minutes Step 8)

Compress the mixture of powders in compressor at a theoretical weight of 375 mg. Approximately 2000 tablets were obtained with the following characteristics:

Average weight 375 mg. (365.63 mg.-384.37 mg)—Fragility less than 0.5%-Breakdown time less than 15 minutes (Medium:water) and they were conditioned in blisters of PVC 250 micron/PVD 60 grams/square meter—Ambar (Aluminium).

Using the same method tablets containing 25, 50 and 100 mg. of diclofenac sodium were produced in the form of microcapsules according to this invention.

The chewable tablets revealed a pleasant taste.

Similar chewable tablets were prepared with enteric microcapsules of diclofenac, diclofenac potassium and diclofenac epolamine.

Clinical Study:

Gastro-intestinal tolerance to gastro-resistant diclofenac chewable tablets in gastrolabile patients with acute muscular-articular pathology The digestive tolerance and efficiency of the chewable tablets containing 50 mg of microencapsulated enteric diclofenac without coating agent aggregate, as active ingredient, was assessed in gastrolabile patients with a background of slight or moderate digestive intolerance to non-steroidal anti-inflammatory drugs (NSAID) and acute muscular-articular pathology, susceptible to treatment with diclofenac.

Methods: Prospective, open, multicentre assay. Walk-in patients with acute muscular-articular pathology and a history of gastric intolerance to NSAIDs. Treatment with chewable diclofenac 50 mg, 1-3 times a day, for 7 to 14 days was indicated. Tolerance was assessed with respect to NSAIDs used before. The efficiency was assessed using a questionnaire on General Patient Impression (PGI) and an Visual Analog Pain Scale (VAS).

Results: 54 patients were assessed. With an average age of 53. A total of 78% of the patients received 150 mg/day and 22% received 100 mg/day. The average treatment time was 10.35±2.84 days. The patients showed good tolerance. The adverse gastric events were observed in 5.55% of the patients treated. According to the PGI questionnaire, 92.45% of the patients referred improvement in pain with the treatment. According to the VAS for pain, the basal value was 6.34+/−1.49 and the post-treatment value 2.01+/−1.40, p<0.01 (according to Student test). In the comparative analysis carried out by patients, with respect to other poorly tolerated NSAIDs used before, 88.68% referred having better tolerance to this new formula of diclofenac in chewable tablets.

Conclusions: The chewable tablets containing 50 mg of diclofenac sodium revealed convenient therapeutic efficiency and the most significant was the tolerance in gastrolabile patients (with previous intolerance to NSAIDs), attributable to the presence in the composition of diclofenac sodium in the form of enteric microcapsules produced according to this invention which can be chewed without losing their property.

Similar chewable tablets were prepared with enteric microcapsules of diclofenac, diclofenac potassium and diclofenac epolamine.

Example XV

Preparing Prolonged Release Microcapsules from Enteric Microcapsules with an Homogeneous Composition Containing Diclofenac Sodium 100 grams of enteric microcapsules of diclofenac sodium with quick releaes at pH 6.8 or higher produced according to EXAMPLE IV above were transformed into prolonged release microcapsules according to the following sequence:

a) were spray coated in Vector equipment Model MFL.01 (Vector Micro Fluid Bed Dryer, Model MFL.01) slowly over 2 hours, with 47 grams of an ethanol-water (95/5%) suspension containing triethyl acetate (1.0%), talc (1.6%) and type B ammonium methacrylate copolymer (Eudragit® RS) (6.36%) under the following operating conditions:

T inlet (suspension inlet temperature) 35° C.

T product (temperature of microcapsules bed) 25-30° C.

Nozzle Air (atomising air pressure) 8.5 psi

Pump Speed (rotation speed of the injection pump) 10-17 rpm

Air Flow (air flow) 70 LPM (liters per minute)

b) the coated and separated microcapsules were subject to 40° C. for 24 hours in a forced air circulation kiln.

c) finally they were conditioned in a hermetically sealed container.

Analytically it was revealed that following treatment for 1 and a half hours in a hydrochloric acid medium (apparatus USP, type 2 (rotors) at 100 rpm and 37° C.) the microcapsules at pH 6.8 (in trisodium phosphate buffer at 100 rpm and 37° C.) release: in 2 hours up to 40% of the diclofenac sodium they contain, in 4 hours up to 70% and in 6 hours more than 80% of their content.

Example XVI

Preparing Oral Multiparticled Capsules Containing 100 mg of Diclofenac Sodium in the Form of Prolonged Release Enteric Microcapsules and 20 mg of Omeprazole in the Form of Pellets 2000 capsules were prepared according to Example VI by adding 100 mg of diclofenac sodium in the form of prolonged release microcapsules produced according to Example XV.

Analytically, the capsules revealed that at pH 6.8 they release: a) in two hours no less than 40% of the diclofenac sodium they contain; b) in four hours the percentage released was higher than 70% and less than 90%; c) in six hours the percentage released in the three batches was higher than 80%.

Example XVII

Preparing Multiparticled Chewable Tablets Containing 100 mg of Diclofenac Sodium in the Form of Prolonged Release Microcapsules Three batches of 2000 chewable tablets containing 100 mg. of diclofenac sodium in the form of prolonged release microcapsules were produced according to the method described in Example XIV using prolonged release microcapsules prepared according to Example XV.

The release percentage of diclofenac sodium at pH 6.8 after two, four and eight hours was similar to that indicated in Example XVI.

The invention claimed is:

1. Oral multiparticled pharmaceutical composition in the form of capsules, powder for suspension in water or chewable tablets comprising: 25 to 100 mg of diclofenac or one of the sodium, potassium or epolamine salts thereof in the form of enteric calcium alginate microcapsules with homogeneous composition, wherein the enteric calcium alginate microcapsules with homogeneous composition consist of: calcium alginate; and diclofenac or one of the sodium, potassium or epolamine salts thereof.

2. Oral multiparticled pharmaceutical composition in the form of chewable tablets according to claim 1, wherein said enteric calcium alginate microcapsules with homogeneous composition do not release more than 2% of diclofenac or one of the salts thereof in an acidic medium over 2 hours under stirring and release no less than 90% of the diclofenac or one of the salts thereof in 30 minutes at pH 6.8 or higher also under stirring.

3. Oral multiparticled pharmaceutical composition in the form of capsules, powder for suspension or chewable tablets according to claim 1, further comprising 10 to 40 mg of a proton pump inhibitor selected from omeprazole, esomeprazole, lanzoprazole and pantoprazole, in the form of pellets with enteric behaviour.

4. Oral multiparticled pharmaceutical composition according to claim 3, wherein the proton pump inhibitor is in the form of omeprazole pellets.

5. Oral multiparticled pharmaceutical composition according to claim 1, wherein the enteric calcium alginate microcapsules with homogeneous composition have a size in the range of 250 microns to 1000 microns.

6. Oral multiparticled pharmaceutical composition according to claim 1, wherein said enteric calcium alginate microcapsules with homogeneous composition are produced with a method comprising the following steps:
A) preparing a solution of an alginate salt, selected from sodium, potassium or ammonium alginate, in water-ethanol and dissolving under stirring in an active ingredient comprising diclofenac or one of the salts thereof in the presence of a surfactant selected from the group consisting of: sorbitan monostearate, sorbitan monooleate, polyoxyethylene sorbitan monostearate, polyoxyethylene sorbitan monooleate, and polyoxyethylene sorbitan monolaurate, and sodium bicarbonate, at a temperature under 60° C.;
B) adding the solution obtained in A) to a solution of calcium chloride, while controlling the temperature under 60° C., throughout the process so as to form microcapsules;
C) resuspending the microcapsules formed and isolated without previous drying in a solution of said alginate salt, at a concentration of between 0.05% and 0.1%, under stirring for 30 to 120 minutes at ambient temperature;
D) separating by filtering, drying and sieving successively through 1000 and 250 micron meshes, selecting for producing the pharmaceutical composition only the fraction of microcapsules obtained and sized between both meshes, wherein the microcapsules obtained and selected have an active ingredient content higher than 55%;
E) and optionally, converting the microcapsules thus obtained into prolonged release microcapsules.

7. Oral multiparticled pharmaceutical composition according to claim 1, wherein said enteric calcium alginate microcapsules with homogeneous composition contain less than 10% of diclofenac crystals.

8. Oral multiparticled pharmaceutical composition according to claim 1, wherein the enteric calcium alginate microcapsules with homogeneous composition further comprise a dried coating, producing prolonged release enteric calcium alginate microcapsules with homogeneous composition.

9. Oral multiparticled pharmaceutical composition according to claim 8, wherein said composition is in the form of chewable tablets comprising 100 mg of diclofenac or one of the salts thereof in the form of prolonged release enteric calcium alginate microcapsules.

10. Oral multiparticled pharmaceutical composition according to claim 8, wherein said composition is in the form of capsules comprising: prolonged release enteric calcium alginate microcapsules of diclofenac or one of the sodium, potassium or epolamine salts thereof; and a proton pump inhibitor in the form of pellets selected from omeprazole, esomeprazole, lanzoprazole, and pantoprazole; in an amount ranging from 10 mg to 40 mg.

11. Oral multiparticled pharmaceutical composition according to claim 1, further comprising prolonged release enteric calcium alginate microcapsules.

12. Oral multiparticled pharmaceutical composition according to claim 11, further comprising a proton pump inhibitor selected from omeprazole, esomeprazole, lanzoprazole and pantoprazole in an amount ranging from 10 mg to 40 mg.

13. Oral multiparticled pharmaceutical composition containing diclofenac or one of the sodium, potassium or epolamine salts thereof in the form of prolonged release enteric calcium alginate microcapsules with homogeneous composition according to claim 8, wherein said prolonged release enteric calcium alginate microcapsules with homogeneous composition are produced according to a method comprising the following steps:
A) preparing a solution of an alginate salt, selected from sodium, potassium or ammonium alginate, in water-ethanol and dissolving under stirring in an active ingredient comprising diclofenac or one of the salts thereof in the presence of a surfactant selected from the group consisting of: sorbitan monostearate, sorbitan monooleate, polyoxyethylene sorbitan monostearate, polyoxyethylene sorbitan monooleate, and polyoxyethylene sorbitan monolaurate, and sodium bicarbonate, at a temperature under 60° C.;
B) adding the solution obtained in A) to a solution of calcium chloride, while controlling the temperature under 60° C., throughout the process so as to form microcapsules;
C) isolating the microcapsules formed without previous drying and resuspending them in a solution of said alginate salt, at a concentration of between 0.05% and 0.1%, under stirring for 30 to 120 minutes at ambient temperature;

D) separating by filtering, drying and sieving successively through 1000 and 250 micron meshes, selecting for producing the pharmaceutical composition only the fraction of microcapsules obtained and sized between both meshes, wherein the microcapsules obtained and selected have an active ingredient content higher than 55%;

E) converting the microcapsules thus obtained into prolonged release microcapsules through the following steps:
  1) coating the enteric calcium alginate microcapsules with homogeneous composition obtained in step D) with a suspension in water-ethanol that contains 0.5% to 1% triethyl acetate, from 1.2% to 1.8% of talc, and between 5.0% and 7.0% of type B ammonium methacrylate copolymer using a spray;
  2) keeping the microcapsules in contact with the suspension, maintaining the temperature of the microcapsules to be coated at 25-30° C. throughout the operation; and
  3) separating the coated enteric calcium alginate microcapsules and drying in a kiln under an air current to obtain prolonged release enteric calcium alginate microcapsules of diclofenac.

* * * * *